United States Patent [19]
Shepard

[11] Patent Number: 4,480,340
[45] Date of Patent: Nov. 6, 1984

[54] INTRAOCULAR LENS WITH RESILIENT SUPPORT MEANS

[76] Inventor: Dennis D. Shepard, 401 E. Palisade, Santa Maria, Calif. 93454

[21] Appl. No.: 235,585

[22] Filed: Feb. 18, 1981

[51] Int. Cl.³ ............................ A61F 1/16; A61F 1/24
[52] U.S. Cl. ............................................................ 3/13
[58] Field of Search ........................................ 3/13, 1

[56] References Cited

U.S. PATENT DOCUMENTS

| | | | |
|---|---|---|---|
| 3,925,825 | 12/1975 | Richards et al. | 3/13 |
| 4,159,546 | 7/1979 | Shearing | 3/13 |
| 4,244,060 | 1/1981 | Hoffer | 3/13 |
| 4,249,271 | 2/1981 | Poler | 3/13 |
| 4,254,510 | 3/1981 | Tennant | 3/13 |

OTHER PUBLICATIONS

"The Intraocular Implant Lens Development and Results with Special Reference to the Binkhorst Lens" (Book), by M. E. Nordlohne, The Williams & Wilkins Co., Baltimore, 1975, pp. 14–20.

Primary Examiner—Ronald L. Frinks
Attorney, Agent, or Firm—Daniel J. Meaney, Jr.

[57] ABSTRACT

An intraocular lens for an eye including a lens body having a first sector end and a second sector end which is adapted to be positioned in relationship to the pupil such as in front of or behind the pupil and two sets of resilient support means wherein each of the resilient support means has one end secured to the lens body around the periphery of the lens within the first sector or the second sector and the other ends of the resilient support means which terminate at an annular shaped guide and support element and wherein each of the resilient support means is secured in the periphery of the lens portion in the first sector end or the second sector end in opposed alignment to each other and positioned at a selected diverging angle relative to the other resilient support means in that sector and wherein the resilient support means extend outwardly from the lens body and in substantially the plane of the lens portion enabling the annular shaped guide and support elements to slideably engage tissue in at least one of the anterior chamber or the posterior chamber of the eye causing the resilient support means to deflect within the plane of the lens body to self-adjust and position the lens body in front of or behind the pupil is shown.

10 Claims, 13 Drawing Figures

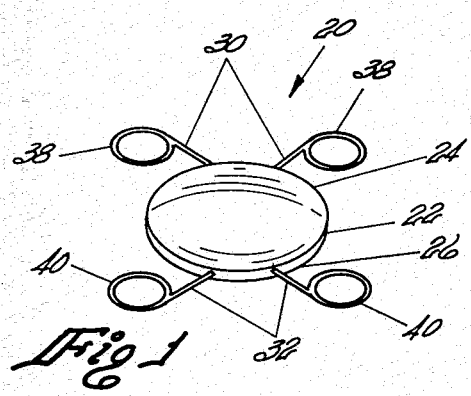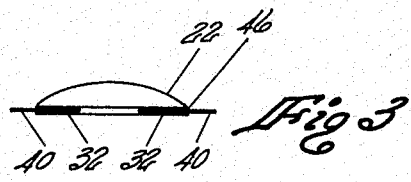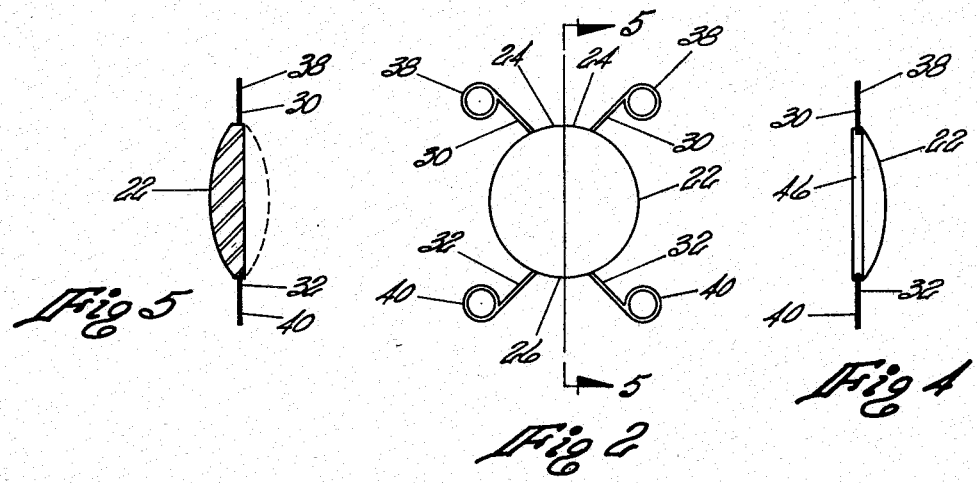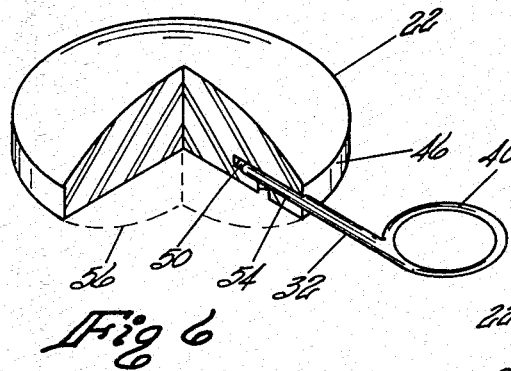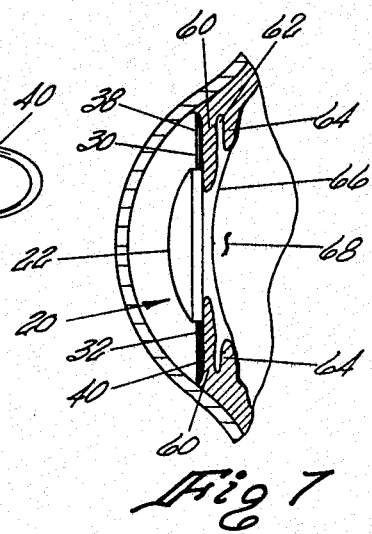

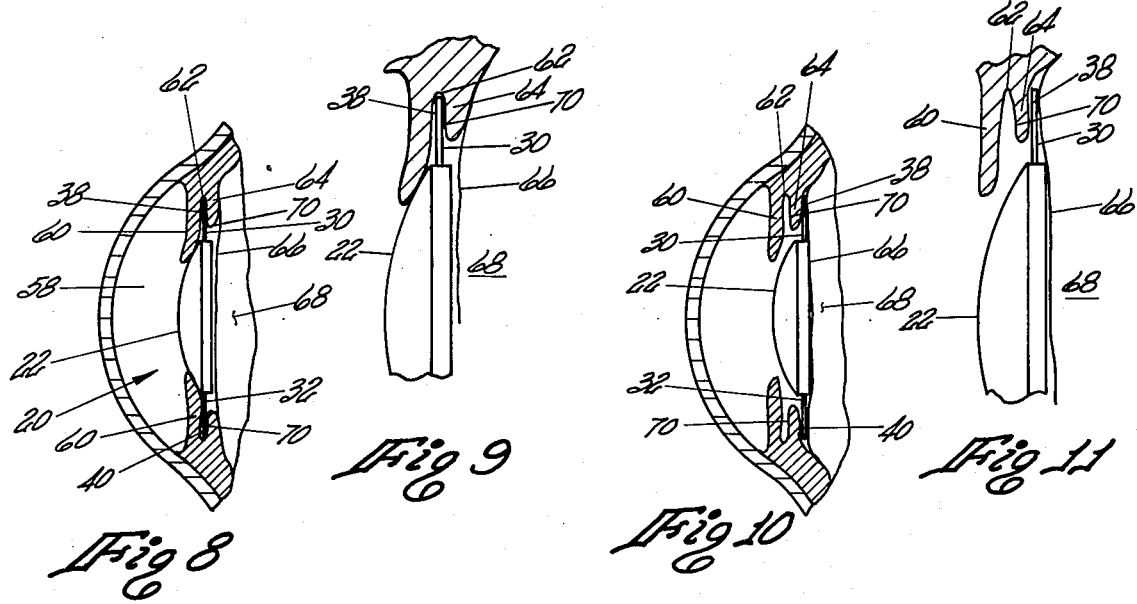
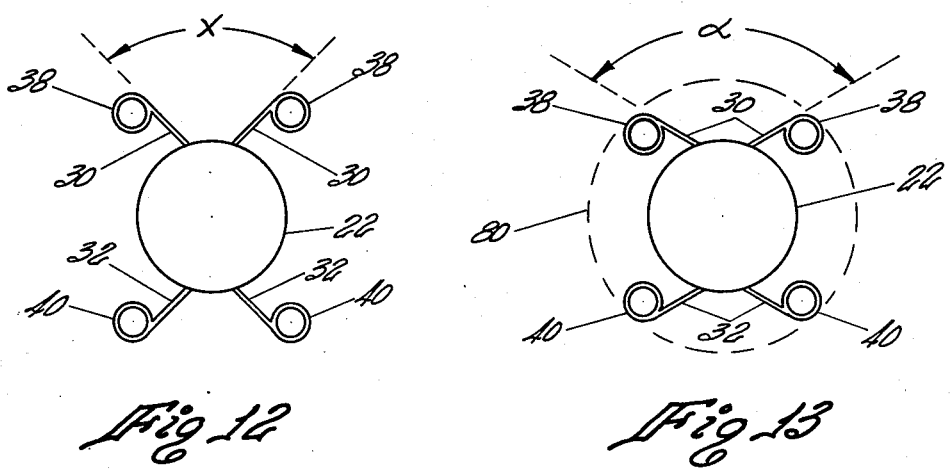

INTRAOCULAR LENS WITH RESILIENT SUPPORT MEANS

BACKGROUND OF THE INVENTION

1. Field of the Invention

This invention relates to an artificial intraocular lens for implantation in either the anterior chamber or posterior chamber of an eye and more particularly relates to an intraocular lens having resilient support means which when inserted into the anterior chamber or posterior chamber of the eye is self-adjusting such that the resilient means supports the lens body in front of or behind the pupil.

2. Description of the Prior Art

It is known in the art to utilize an artificial intraocular lens which is located in either the anterior chamber or posterior chamber of a human eye during cataract surgery.

Typical artificial intraocular lenses which can be located in the anterior chamber of an eye are disclosed in U.S. Pat. Nos. 3,971,073; 4,134,161 and 4,174,543.

Typical known prior art artificial lenses which are adapted to be located in the posterior chamber of an eye are disclosed in U.S. Pat. Nos. 3,711,870; 3,866,249; 4,159,543 and 4,014,149.

U.S. Pat. No. 4,134,161 discloses an adjustable intraocular lens having an optical lens portion and an adjustable member which includes a projecting element and a wedging piece which are forced toward each other causing fixation of the lens portion in the anterior chamber of a human eye.

U.S. Pat. No. 4,174,543 discloses an intraocular lens adapted for placement into the anterior chamber of the eye and comprising a lens body and two pairs of contact lobes with at least one pair being capable of yielding independently of the other pair and which responds to normal distortion of the eye wherein each of the contact lobes deflects independently of the other contact lobe in a direction toward and away from the lens body.

In the intraocular lens disclosed in U.S. Pat. No. 4,159,543, a lens body having curved looped strands, one of which is secured in the lens body and the other of which extends outwardly therefrom and terminates in an arch portion to present a rounded strand surface for being merged against or butting the ciliary body or muscle in the eye when the lens is located in the posterior chamber is disclosed.

In the intraocular lens structure disclosed in U.S. Pat. No. 4,159,543, FIG. 9 discloses three strands having rounded ends thereof which are essentially positioned equidistantly around the lens body. When the artificial intraocular lens is located in the posterior chamber of the human eye, the resilient action of the spring-like strands cause the same to be biased to urge the rounded ends thereof against the ciliary body to achieve centering and fixation of the lens to the pupil.

SUMMARY OF THE INVENTION

This invention relates to a novel, unique and improved intraocular lens for an eye comprising a lens portion having a first sector end and a second sector end which is adapted to be positioned either in front of or behind the pupil of the eye, even in the absence of the posterior lens capsule. The intraocular lens includes two sets of resilient support means wherein each of the resilient support means has one end secured to the lens portion in at least one of the first sector end and the second sector end and the other end of which terminates in an annular shaped guidance support element. One of the two sets of resilient support means are secured in the first sector end of the lens portion and the other of the two sets of resilient support means are secured in an opposed alignment in the second sector end. Each of the resilient support means are secured in the respective sector end at a selected diverging angle relative to the other resilient support means of that set. Each of the resilient support means has associated annular shaped guide and support elements extending outwardly from the lens portion and in substantially the plane of the lens. The annular shaped guide and support elements are adapted to slideably engage tissue in at least one of the anterior chamber or posterior chamber of an eye causing the resilient support means to deflect within the plane of the lens portion to self-adjust and position the lens portion in front of or behind the pupil respectively.

In performing cataract surgery, the intraocular lens of the present invention is to be placed inside the human eye after removal of a cataract. In performing a cataract operation wherein the intraocular lens is to be positioned in the anterior chamber, the physician must determine the proper eye correction required and must also measure the eye dimensionally to specify the diametral length required of the lens body. The physician would typically specify the diametral length in the appropriate diopter correction and order the lens in that diameter and an additional two lenses with greater and lesser diametral length, one with a length of 0.5 millimeters longer and one with a length of 0.5 millimeters shorter. For example a physician may determine that a patient requires a +19.5 diopters correction and that the ideal dimensional length would be 12.5 millimeters. The physician would normally order three lenses which would typically include the following: (a) +19.5 diopters×12.0 millimeters; (b) +19.5 diopters×12.5 millimeters; and (c) +19.5 diopters×13.0 millimeters.

During surgery, and after removal of the cataract by either intracapsular or extracapsular procedure, the physician would then perform a test in the anterior chamber to see if the selected intraocular lens was ideally sized or if it was either too loose or too tight. The ultimate sizing and implantation would be accomplished using the intraocular lens having the proper diopter correction and diametral length as described above.

In the known prior art devices, the intraocular lenses are designed to be located either specifically in the anterior chamber or posterior chamber of an eye. Certain of the known prior art artificial intraocular lenses include means in the form of strands or contact lobes which are designed to permit movement of a lens body in the intraocular lens relative to a support means which supports the intraocular lens within the chamber of the eye.

None of the known prior art artificial intraocular lenses are adapted to be located in either the anterior chamber or posterior chamber of an eye to be determined by a surgeon while performing cataract surgery. In the present invention, the resilient support means includes two sets of resilient support means which are positioned in the periphery of the lens body in a predetermined relationship to each other and to the lens body to afford resilient support of the lens to position the lens body in front of or behind the pupil and to permit compression and deflection of the resilient support means in the plane of the lens body in the manner where the center of the lens body does not move axially in a sagital relation to the eye containing it in response to the circumferential force placed thereon by the deflection of the resilient support means in centering and positioning a lens body within the eye.

One advantage of the present invention is that the intraocular lens with resilient support means can be positioned in either the anterior chamber or posterior chamber of an eye as determined by a surgeon during surgery.

Another advantage of the present invention is that an intraocular lens having a lens body with a proper diopter correction and approximate diametral length can be utilized during cataract surgery thereby avoiding the necessity of having available an additional intraocular lens of one size smaller and one size larger in diametral length.

Still yet another advantage of the present invention is that when an intraocular lens with resilient support means has been located in the anterior chamber or posterior chamber of a patient, the self-adjusting feature of the intraocular lens relative to the ocular support structures posterior to the scleral spur by deflection of the resilient support means provides less trauma to the eye.

A further advantage of the present invention is that the intraocular lens with resilient support means is self adjusting so as to position the lens relative to the pupil independent of the dimensional restraints of the eye.

A still yet further advantage of the present invention is that the intraocular lens having resilient support means can be produced in a fewer number of diametral lengths for each diopter correction required which reduces the number of intraocular lenses required to be carried by a hospital, medical distributor, surgeon and the like.

An additional advantage of the present invention is that the intraocular lens with resilient support means can be fully supported in the anterior chamber of an eye after prior removal of segments of iris tissue, such as after glaucoma surgery, and can therefore be placed in an eye that has had prior cataract removal in the past, e.g. a secondary implantion.

BRIEF DESCRIPTION OF THE PRESENT INVENTION

The foregoing and other advantages of this invention will be apparent from the following description of the preferred embodiment of the invention when considered with the illustrations and accompanying drawing which includes the following figures:

FIG. 1 is a perspective view of an intraocular lens having resilient support means of the present invention;

FIG. 2 is a front plan view of an intraocular lens of the present invention;

FIG. 3 is a top plan view of an intraocular lens of the present invention;

FIG. 4 is a right end plan view of an intraocular lens of the present invention;

FIG. 5 is a sectional view of the intraocular lens taken along section lines 5—5 of FIG. 2;

FIG. 6 is a pictorial representation of a portion of the lens body cut away to show the means of securing a resilient support means within the lens body;

FIG. 7 is a diagrammatical representation showing an intraocular lens with a resilient support means implanted within the anterior chamber of an eye;

FIG. 8 is a pictorial representation of an intraocular lens implanted within the posterior chamber of an eye and located between the iris and ciliary processes (posterior chamber);

FIG. 9 is partial end plan view portion cross-section showing the location of the annular shaped guide and support elements between the iris and ciliary processes (posterior chamber);

FIG. 10 is a perspective view showing the intraocular lens implanted within the lens capsular bag between the ciliary processes and end of the hyaloid membrane and/or posterior lens capsule;

FIG. 11 is a partial end plan view portion cross-section showing the relationship between the annular shaped guide and support elements between the ciliary processes, the lens capsular bag and end of the hyaloid membrane and/or posterior lens capsule;

FIG. 12 is a front plan view showing the selected angle between one set of the resilient support means secured in a sector end on the periphery of a lens body; and FIG. 13 is a diagrammatic representation of the deflection of a set of the resilient support means showing the increase of the selected angle therebetween due to the deflection of the resilient support means when the intraocular lens is implanted in the anterior chamber or posterior chamber of an eye.

DESCRIPTION OF THE PREFERRED EMBODIMENT

FIG. 1 illustrates an intraocular lens 20 which is formed of a lens portion or lens body 22 having a first sector end 24 and a second sector end 26. The lens body 22 of the intraocular lens 20 is adapted for positioning over a pupil.

The intraocular lens 20 includes two sets of resilient support means 30 and 32. Each of the resilient support means 30 and 32 has one end thereof secured to the lens body 22 in at least one of the first sector ends 24 and the second sector ends 26. The other end of each of the resilient support means terminates in the annular shaped guide support elements 38 which, in the preferred embodiment, are circular shaped guide elements located at one end of the resilient support means 30. Annular shaped guide and support elements 40 of similar construction are located at the other end of each of the resilient support means 32 which are secured in the second sector end. In the preferred embodiment, the resilient support means includes an elongated strand which terminates in a circular shaped strand.

Each set of the resilient support means 30 and 32 is secured in opposed alignment in the periphery of the lens body 22. Each of the resilient support means is secured in its respective sector at a selected diverging angle relative to the other resilient support means of that set. Each of the annular shaped guide and support elements 38 of the resilient support means 30 and annular guide and support elements 38 and 40 of the resilient support means 32 extend outwardly from the lens body 22 circumferentially from and in substantially the plane of the lens body 22. The annular shaped guide and support elements 38 and 40 are adapted to slideably engage tissue in either the anterior chamber or the posterior chamber of an eye. When the annular shaped guide and support elements 38 and 40 engage such tissue, the resilient support means deflect within the plane of the lens body to self-adjust and position the lens body 22 over the pupil.

FIGS. 2, 3 and 4 illustrate in greater detail the structural relationship between the lens body 22, the resilient support means 30 and 32 and its associated annular shaped guide support elements 38 and 40, respectively. As illustrated in FIG. 2, the annular shaped guide and support elements at the other end of each resilient support means 30 and 32 terminate in a circular element wherein the shape or the periphery thereof is rounded to permit the annular shaped guide and support elements 40 to engage tissue in the chamber with substantially the same rounded surface independent of the amount of deflection of the resilient support means.

As illustrated in FIGS. 3 and 4, the lens body 22 includes a flat edge 46 which extends around the periphery of the lens body 22 through which the one end of the resilient support means is secured to the lens body 22.

FIG. 5 shows that the surface of the lens body 22 in the preferred embodiment is plano-convex in shape, but it may be bi-convex as shown in FIG. 6.

Also, as illustrated in FIG. 2, the lens body 22 is circular in shape in the preferred embodiment.

FIG. 6 shows a cut-away pictorial representation of the lens body 22 with flat edge 46, extending around the periphery thereof. An aperture 50 is formed therein at a predetermined location in the first or second sector each of the lens body 22 and is adapted to receive one end of the resilient support means 32. FIG. 6 illustrates that one end 54 of the resilient support means 32 is secured therein. The annular shaped guide and support element 40 extends outwardly from the flat edge 46 of the lens body 22. In addition, FIG. 6 illustrates by dashed lines 56 that the lens body can have a bi-convex surface as an alternate embodiment. Any number of well known means may be used to secure the ends of the resilient support means within the lens body 22. For example, the resilient support means can be secured by pressure fit, adhesive, heat sealed, or if a metal-centered means, by heating and inserting the same into a plastic lens body.

FIG. 7 illustrates the intraocular lens of the present invention implanted in the anterior chamber of a human eye. In FIG. 7 the intraocular lens 22 is positioned with the plano-convex surface extending inwardly into the anterior chamber such that the lens body 22 is centered within the pupil. The resilient support members 30 and its annular shaped guide and support element 38 and the resilient support means 32 and its annular shaped guide and support element 40 are located adjacent the iris 60 of the eye. Behind the lens body 22 is the hyaloid membrane 66 which maintains vitreous humor 68 within the eye. The iris 60 and the ciliary processes 64 define the iridiocapsular cleft 62 which is located in the posterior chamber of the eye.

FIG. 8 illustrates the implantation of the intraocular lens 20 in the posterior chamber of the eye. Typically, the resilient support means 30 and 32 and their associated annular shaped guide and support elements 38 and 40, respectively, are located in the iridiocapsular cleft 62 located between the iris 60 and the ciliary processes 64. The hyaloid membrane 66 has an end 70 which is attached to the ciliary processes 64.

In FIG. 8, the intraocular lens 20 is positioned with the lens body 22 centered within the pupil. The iris 60 and the ciliary processes 64 support the annular shaped guide and support element 38 located at one end of the resilient support means 30 therebetween. The hyaloid membrane 66 extends behind the lens body 22.

FIG. 9 shows in greater detail the annular shaped guide and support element 38 positioned within the iridiocapsular cleft 62 located between the iris 60 and the ciliary processes 64.

FIG. 10 shows an alternate method for locating the intraocular lens of the present invention in the posterior chamber of the eye. As noted herein, the end 70 of the hyaloid membrane 66 is attached to the ciliary processes 64. The surgeon can separate the end 70 at a predetermined location from the ciliary processes 64 and insert the annular shaped support elements 38 and 40 between the ciliary processes 64 and the end 70 of the hyaloid membrane 66.

FIG. 11 shows in greater detail the relationship between the ciliary processes 64 and the end 70 of the membrane 66 which receives the annular shaped guide and support element 38 of a resilient support means 30 in the space formed between the end 70 and the ciliary processes 64 by the surgeon during surgery.

FIG. 12 illustrates pictorially that the resilient support means 30 which terminate in the circular shaped elements 38 are positioned at an obtuse angle "x" relative to each other. In the preferred embodiment, the angle "x" is selected as an obtuse angle which in the preferred embodiment may be between 90 degrees and 120 degrees. However, the preferred selected diverging angle is approximately 90 degrees.

FIG. 13 illustrates pictorially the deflecting action of the resilient support means 30 relative to each other when the circular shaped elements 38 and 40 engage tissue in either the anterior or posterior chamber of an eye as described in connection with FIGS. 7 through 11, inclusive. When the resilient support means 30 are deflected, they are deflected away from their associated resilient support means in the same set and toward the adjacent resilient support means of the other set. The diameter defined by the rounded surfaces of the circular shaped element of the deflected resilient support means is illustrated by dashed line 80 and is smaller than that defined by the same in an undeflected position.

As is shown in FIG. 13, the lens body 22 is positioned and centered in the pupil of the eye, and by action of the resilient support means in response to movement of a patient or of the eye, centers and positions the lens body 22 in the center of the pupil independent of movements of the eye or of any dimensional anomalies thereof.

When an intraocular lens with resilient support means is located in the patient's eye, movement of the patient during running, walking or other activities results in the resilient support means 30 and 32 flexing relative to each other to self-adjust and maintain the lens body 22 within the center of the pupil.

In the preferred embodiment, the lens body is formed of a plastic material, preferably a non-biodegradable plastic material. One such material used for fabricating the lens body may be polypropylene or other material which can be tolerated by a human body when implanted. Also, chemically pure polymethylmethacrylates or other biologically inert polymeric materials may be used. The material used for forming the resilient support means may be formed of any material which may either be a plastic or metal material.

In the preferred embodiment, the resilient support means was formed with polypropylene. A typical diameter of an intraocular lens as defined by the rounded surface of the annular shaped element would be in the order of 13.5 millimeters. A typical diameter of a lens body may be 6 millimeters. In the preferred embodiment, the annular shaped guide and support members may be formed of a circular shaped element having a diameter of approximately 1.1 millimeters.

In fabricating the lens body, it is anticipated that any inert material such as glass, ceramic, non-biodegradable plastic or a combination thereof may be utilized as the lens body. Likewise, the resilient support means may be formed of an appropriate metal or of non-biodegradable plastic material or any combination thereof, to form the resilient support means having the annular shaped guide and support elements extending therefrom.

What is claimed is:

1. An intraocular lens adapted to be located in either the anterior chamber or posterior chamber of an eye and which is adapted to be positioned over the pupil of an eye in a proper optical relationship, said intraocular lens comprising a lens body having a first sector end and a second sector end and a central portion adapted to be positioned over the pupil of an eye;

four resilient support members, each of which has an elongated deflectable strand which has one end thereof which terminates in an annular shaped guide and support member having an enlarged extended surface defining a curved path which includes a portion extending towards the lens body and the other end of which is secured in a predetermined position on the periphery of the lens body in at least one of the first sector end and second sector end, two of said resilient support members being secured in the first sector end on the periphery of said lens body and the other two of said resilient support members being secured in opposed alignment on the periphery of said lens body in the second sector end, each of said resilient support members being positioned with that portion of the one end extending towards the lens body relative to that portion of the one end extending towards the lens body of the other resilient support member located in the same sector end such that the curved path of each portion is located in an opposed direction away from the curved path of the portion of the other resilient member in its respective sector end and secured at its other end in its respective sector end at a selected diverging angle relative to the other resilient support member secured in the same sector end with each of said annular shaped guide and support elements extending outwardly therefrom in substantially the plane of the lens portion, said annular shaped guide and support elements being adapted to slidably engage tissue in at least one of an anterior chamber and posterior chamber of an eye applying a circumferential force onto and deflecting said resilient support member within the plane of the lens body to control movement thereof relative to and around the center of the pupil to self-adjust that portion of the lens body relative to the pupil in a proper optical relationship.

2. The intraocular lens of claim 1 wherein said selected angle is an acute angle and said resilient support means in each set deflect away from the resilient support means of that set and towards the adjacent resilient support means of the other set.

3. The intraocular lens of claim 1 wherein each of said annular shaped guide and support elements at the other end of each resilient support means terminates in a circular element wherein the shape of the periphery thereof which is adapted to engage tissue in a said chamber is substantially the same independent of the amount of deflection of the resilient support means supporting said circular element.

4. The intraocular lens of claim 1 wherein the lens portion is formed of a non-biodegradable plastic material.

5. The intraocular lens of claim 1 wherein the surfaces of the lens portion are plano-convex in shape.

6. The intraocular lens of claim 1 wherein said resilient support means are formed of a non-biodegradable plastic material.

7. The intraocular lens of claim 1 wherein the lens portion has a bi-convex surface.

8. The intraocular lens of claim 1 wherein the lens portion is circular in shape.

9. An intraocular lens adapted to be surgically implanted in either the anterior chamber or posterior chamber of an eye, wherein the intraocular lens includes a lens body having a first sector end and a second sector end which is adapted to be positioned over the pupil of an eye, characterized by:

not more than four resilient support members, each of which has an elongated deflectable strand which has one end thereof which terminates in an annular shaped guide and support member having an enlarged extended surface defining a curved path which includes a portion extending towards the lens body and the other end of which is secured in a predetermined position on the periphery of the lens body selected pattern in at least one of the first sector end and second sector end, two of said resilient support members being secured in the first sector end on the periphery of said lens body and the other two of said resilient support members being secured in opposed alignment on the periphery of said lens body in the second sector end, each of said resilient support members being positioned with that portion of the one end extending towards the lens body relative to that portion of the one end extending towards the lens body of the other resilient support member located in the same sector end such that the curved path of each portion is located in an opposed direction away from the curved path of the portion of the other resilient member in its respective sector end and secured at its other end in its respective sector end at a selected diverging angle relative to the other resilient support member secured in the same sector end with each of said annular shaped guide and support elements extending outwardly therefrom in substantially the plane of the lens portion, said annular shaped guide and support elements being adapted to slidably engage tissue in at least one of an anterior chamber and posterior chamber of an eye applying a circumferential force onto and deflecting said resilient support member within the plane of the lens body to control movement thereof relative to and around the center of the pupil and to self-adjust that portion of the lens body relative to the pupil in a proper optical relationship.

10. An intraocular lens adapted to be located in either the anterior chamber or posterior chamber of an eye wherein the lens body has a first sector end and a second sector end and the lens body is adapted to be positioned over the pupil of an eye in a proper optical relationship, said lens body having resilient support members extending outwardly in the plane of the lens from the periphery of the first sector end and the second sector end, said intraocular lens being characterized in that:
at least two of said resilient support members are located in at least one of the first sector end and second sector end wherein each of said resilient support members is in the form of an elongated deflectable strand having one end thereof which terminates in an annular shaped guide and support member having an enlarged extended surface defining a curved path which includes a portion extending towards the lens body and the other end of which is adapted to be secured in a predetermined position in at least one of said first sector end and said second sector end on the periphery of the lens body, said at least two resilient support members each having the other end thereof secured within the same sector end in said lens body and positioned at a selected diverging angle relative to each of said other ends and with each of said one ends, which terminate in said annular shaped guide and support members enlarged extended surface defining a curved path, being positioned with the portion thereof extending towards the lens body being substantially coplanar with the lens body and with each of the curved paths being located in an opposed direction away from the other of said two resilient support members located on the same sector end, said enlarged extended surface defining the curved path being adapted to slidably engage tissue in at least one of an anterior chamber and posterior chamber of an eye applying a circumferential force onto and deflecting said resilient support members within the plane of the lens body which is adapted to position and center the lens body and to control movement thereof relative to and around the center of the pupil and to provide self-adjusting and maintaining of the lens body relative to the pupil in a proper optical relationship independent of movements of the eye.

* * * * *